United States Patent
van Lummel

[11] Patent Number: 6,165,143
[45] Date of Patent: Dec. 26, 2000

[54] METHOD FOR MEASURING AND INDICATING THE EXTENT TO WHICH AN INDIVIDUAL IS LIMITED IN DAILY LIFE ACTIVITIES

[76] Inventor: R. C. van Lummel, Raamweg 43, 1596 HN Den Haag, Netherlands

[21] Appl. No.: 09/270,719

[22] Filed: Mar. 17, 1999

[30] Foreign Application Priority Data

Mar. 17, 1999 [NL] Netherlands ............................ 1008619

[51] Int. Cl.[7] ............................ A61B 5/103; A61B 5/117
[52] U.S. Cl. ............................................. 600/595; 600/587
[58] Field of Search ...................................... 600/587, 595

[56] References Cited

U.S. PATENT DOCUMENTS

| | | | |
|---|---|---|---|
| 4,882,677 | 11/1989 | Curran .................................... | 600/587 |
| 5,080,105 | 1/1992 | Thornton ................................. | 600/595 |
| 5,163,440 | 11/1992 | DeLuca et al. ......................... | 600/587 |
| 5,263,491 | 11/1993 | Thornton ................................. | 600/587 |
| 5,313,968 | 5/1994 | Logan et al. ............................ | 600/595 |
| 5,375,610 | 12/1994 | LaCourse et al. ...................... | 600/595 |
| 5,885,231 | 3/1999 | Cramer et al. .......................... | 600/595 |
| 5,919,149 | 7/1999 | Allum ...................................... | 600/595 |
| 5,980,429 | 11/1999 | Nashner ................................... | 600/595 |

FOREIGN PATENT DOCUMENTS

| | | | |
|---|---|---|---|
| 0 791 328 A1 | 8/1997 | European Pat. Off. ............... | 600/587 |
| WO 96/04848 | 2/1996 | WIPO . | |
| WO 96/29006 | 9/1996 | WIPO . | |
| WO 96/29007 | 9/1996 | WIPO . | |
| WO 97/41775 | 11/1997 | WIPO . | |

OTHER PUBLICATIONS

Busser, et al., "De Dynaport ADL monitor," Klinische Fysica, nr. 4, 1995, pp. 9–13. Translation enclosed.

Johanson, et al., "A Self–Administered Hip–Rating Questionnaire for the Assessment of Outcome after Total Hip Replacement," The Journal of Bone and Joint Surgery, vol. 74–A, No. 4, Apr. 1992, pp. 587–597.

Wright, et al., "The Patient–Specific Index: Asking Patients What They Want," The Journal of Bone and Joint Surgery, vol. 79–A, No. 7, Jul. 1997, pp. 974–983.

*Primary Examiner*—Eric F. Winakur
*Assistant Examiner*—Charles Marmor, II
*Attorney, Agent, or Firm*—Merchant & Gould P.C.

[57] ABSTRACT

A method for measuring and numerically indicating the extent to which an individual is limited in daily life activities, comprising measuring, with the aid of at least one sensor to be fastened to the body of the individual to be examined, postures, movements and/or motional changes of the body and/or parts of the body of the individual in a selected number of motor activities to be performed by the individual, wherein the measuring data of the sensor are inputted into a computing device and are subsequently compared to corresponding reference data inputted into the computing device, coming from one or more standard groups, in order to determine per measurement or series of measurements a percentage indicating the extent to which the individual is limited as regards the activity in question.

16 Claims, 5 Drawing Sheets

FIG. 2

NAME
AGE
GENDER
OPERATION DATE
SURGEON
TEST DATE       ...
EXAMINER        ...

| DYNAPORT KNEESCORE SUMMARY | PRE | 3m | 6m | 12m |
|---|---|---|---|---|
| KNEESCORE | 31% | — | — | — |
| DATE | ... | | | |

DYNAPORT KNEETEST OVERVIEW

| LOCOMOTION | 3m | 6m | 9m | OUTSIDE | AVERAGE |
|---|---|---|---|---|---|
| WALKING | | | 31% | 0% | 16% |
| INTERVAL | 54% | 52% | 46% | | 51% |
| CURVE | | | 37% | | 37% |
| AVERAGE | 54% | 54% | 52% | 0% | |
| | | | | SCORE | 29% |

| RISE & DESCEND | A SIDE | NA SIDE | | | AVERAGE |
|---|---|---|---|---|---|
| STAIRS | 27% | 34% | | | 31% |
| SLOPE | 24% | 41% | | | 33% |
| STEP 20 cm | 23% | 62% | | | 43% |
| STEP 30 cm | 28% | 0% | | | 14% |
| STEP 40 cm | 0% | 0% | | | 0% |
| AVERAGE | 20% | 32% | | | |
| | | | | SCORE | 25% |

| TRANSFERS | A SIDE | NA SIDE | — | | AVERAGE |
|---|---|---|---|---|---|
| BEND | 37% | 33% | | | 35% |
| SIT 40 cm | | | 46% | | 46% |
| SIT 30 cm | | | 30% | | 30% |
| SIT 20 cm | | | 0% | | 0% |
| LYING | | | 49% | | 49% |
| AVERAGE | 37% | 33% | 31% | | |
| | | | | SCORE | 36% |

| LIFT AND MOVE LOADS | A SIDE | NA SIDE | 9m | | AVERAGE |
|---|---|---|---|---|---|
| LIFT | 37% | 33% | | | 35% |
| PUSH | | | 37% | | 37% |
| PULL | | | 44% | | 44% |
| TRAY | | | 30% | | 30% |
| AVERAGE | 37% | 33% | 37% | | |
| | | | | SCORE | 35% |

DYNAPORT KNEESCORE  31%

METHOD FOR MEASURING AND INDICATING THE EXTENT TO WHICH AN INDIVIDUAL IS LIMITED IN DAILY LIFE ACTIVITIES

This invention relates to a method for measuring and indicating the extent to which an individual is limited in daily life activities.

Such a method is known from the article "A Self-Administered Hip-Rating Questionnaire for the Assessment of Outcome after Total Hip Replacement" in The Journal of Bone and Joint Surgery, vol. 74-A, no. 4, April 1992, pp. 587 ff. The known method utilizes a questionnaire through which patients who have had a hip operation are questioned at set times. The questions concern the clinical condition of the patient. The answers obtained are graded in a scale to indicate the extent of limitation in daily life activities. A drawback of this known method is that the outcome merely reflects something of the patient's perception, and the rating thereof (the assessment thereof) by the physician. The method thus does not lead to an objective measure and the result has only limited utility. Thus far, however, the search for a solution to the problem outlined has been focused virtually exclusively on an improvement of the formulation of the questions. See, for instance, the article "The Patient-Specific Index: Asking Patients What They Want" in The Journal of Bone and Joint Surgery, vol. 79-A, 1997, pp. 974–983.

The object of the present invention is to provide a method by which the extent of limitation in daily life activities can be measured and indicated in a more objective manner.

The stated object is achieved, in accordance with the invention, through a method which comprises measuring, with the aid of at least one sensor to be fastened to the body of the individual to be examined, postures, movements and/or motional changes of the body and/or parts of the body of the individual in a selected number of motor activities to be performed by the individual, wherein the measuring data of the at least one sensor are inputted into a suitably programmed computing device, where those data, as far as necessary, are converted into data concerning position and/or movement and/or motional change of the body and/or parts of the body, and are subsequently compared to corresponding reference data inputted into the computing device, coming from one or more standard persons and/or standard groups, in order to determine per measurement or series of measurements a percentage or ratio indicating the extent to which the individual is limited as regards the activity in question.

U.S. Pat. No. 5,375,610 discloses a method for measuring and indicating the functional mobility of an individual. The different positions of the body or parts of the body of a disabled individual are compared to corresponding positions of able-bodied individuals. For measurement, the individual to be examined must wear a body suit, fitting the body closely, in which sensors are incorporated at a large number of points. The measuring apparatus available for this known method provides a graphic representation of the activity profile of the subject and reference persons. Also provided is a possibility for analysis, whereby tables of data concerning different body positions of different individuals are compared and an error percentage is computed and displayed. Essentially, the known method is a descriptive one. The qualitative assessment is left to the user of the method and the associated apparatus. From the multiplicity of data produced, the user must draw conclusions. A disadvantage of the method known from U.S. Pat. No. 5,375,610 is further that the individuals to be examined must wear a body suit, which fits the body closely. This gives the subjects a feeling of unfreedom.

International patent application WO 97/41775 discloses a method for evaluating, reducing and managing injuries. In that method, using measuring apparatus to be worn by a subject, data of that subject concerning Inter alia position and movement of the body and/or parts of the body of the subject are gathered. The data gathered are processed in a computing device and analyzed to come to a determination of the functional condition or suitability of the subject. How all this works and what exactly is determined is not indicated in the publication. Reference is made only to various kinds of "Analysis Software". A specific ratio, as is determined in the method according to the present invention, is not mentioned in the publication.

Accordingly, the idea underlying the invention is to obtain in a standardized test objective measuring data of the total motor apparatus of an individual to be examined at the level of the limitation, and to use same for determining a ratio or score expressing the limitation in the daily life activities. Upon application of the method according to the invention to healthy standard persons and patients having knee prostheses, it was found that with the scores obtained, a clear discrimination can be made between healthy individuals, good and poor patients, and patients shortly after and long after the operation. The scores obtained thus provide clues for further treatment. The method according to the invention is suitable to be used in respect of all kinds of limitations in daily life activities. Mentioned above, by way of example, were patients having knee prostheses. Equally, patients having a hip prosthesis, having a dysfunction of the ankle joint, or having back complaints can be considered.

The standard persons and/or standard groups which provide the reference data can be, for instance, a reference group of persons without the complaints/problems in question and/or a reference group of persons having comparable complaints to the individual to be examined but not having been treated/operated yet.

By daily life activities are commonly meant the various motor activities that constitute the basis for an individual to manage independently. Limitation in the activities is commonly understood to mean a limited skill. The generally adopted terminology regarding the motor apparatus is operationalized in three levels: disturbance (the disturbed function), limitation (the limited skill) and handicap (handicapped in role fulfillment). Medical therapy is usually aimed at improving the functions with a view to accomplishing an improvement at the level of the skills. The method according to the invention provides for measurements at the level of the limitation (for instance, the ability to get up from a chair) and not at the level of the disturbance (for instance, dysfunction of the knee joint).

In the method according to the invention, the gross motor activity of the individual to be examined is recorded under highly faithful, everyday circumstances, while nonetheless the posture and movement of the body and the parts of the body are determined with a high degree of accuracy. Measuring the gross motor activity can occur, for instance, in the manner as described in EP-A-0 791 328. The method according to the invention further provides a status overview, consisting of the computed scores, of the limitation on the motor apparatus, for diagnostic purposes and, for instance, for evaluation of medical therapy in the medical disciplines of orthopedics, physiotherapy and rehabilitation.

It is noted that a method in which, on the basis of measuring data, different parameters are combined into an overall score for the condition or dysfunction of a part of the body is known from international patent application WO 96/29006. In this known method, the measurements take place at the level of the disturbance and it is not possible to use the score at the level of the limitation.

In a suitable embodiment of the method according to the invention, for a number of physical activities, preferably of the kind that is performed daily, and divided over a number of main functions, ratios are determined for a number of movement characteristics per activity and then averaged at least per activity, in order to determine for each of those activities a percentage or ratio, followed by determining from the ratios of activities belonging to one main function a ratio for that main function, and determining from the ratios for each of the number of main functions one total percentage or total ratio that is representative of the total limitation in daily life activities (the total function) of the individual in question, The number of movement characteristics per activity is preferably at least three, but more preferably a large number, up to as many as 10 or more. The measuring data concerning movement characteristics can be of different natures. Movement characteristics that could be measured are, for instance, the intensity, the velocity, the angular change, the step frequency, the step phases, and the push-off acceleration. Of importance is that the method according to the invention can yield a single score concerning the total function of the individual under examination. If this were not possible, the method according to the invention would not have been clinically useful. In none of the above-discussed methods is it possible to arrive at such a score concerning the total function.

Preferably, according to the invention, the measurements are performed on activities selected from at least each of the groups (main functions) of locomotion, rise and descend, transfer (change of body posture), lifting and moving loads. Suitably, the measurements are then performed on activities at least comprising walking, climbing stairs, descending stairs, sitting down in a chair, getting up from a chair, lying down on a bed, getting up from a bed, lifting an object and carrying an object.

In another suitable embodiment of the method according to the invention, the measurements are performed with at least two sensors to be fastened to the body of the individual to be examined. Preferably, use is made of a sensor fitted in a strap to be fitted around the waist of the individual under examination, and of a sensor fitted in a strap or other element to be fastened to a lower or upper leg of the individual to be examined.

The invention will be elucidated with reference to the drawings, in which;

FIG. 2 shows an example of a score table for an examination on the condition of the knee joint(s) of a subject;

Figure 1:
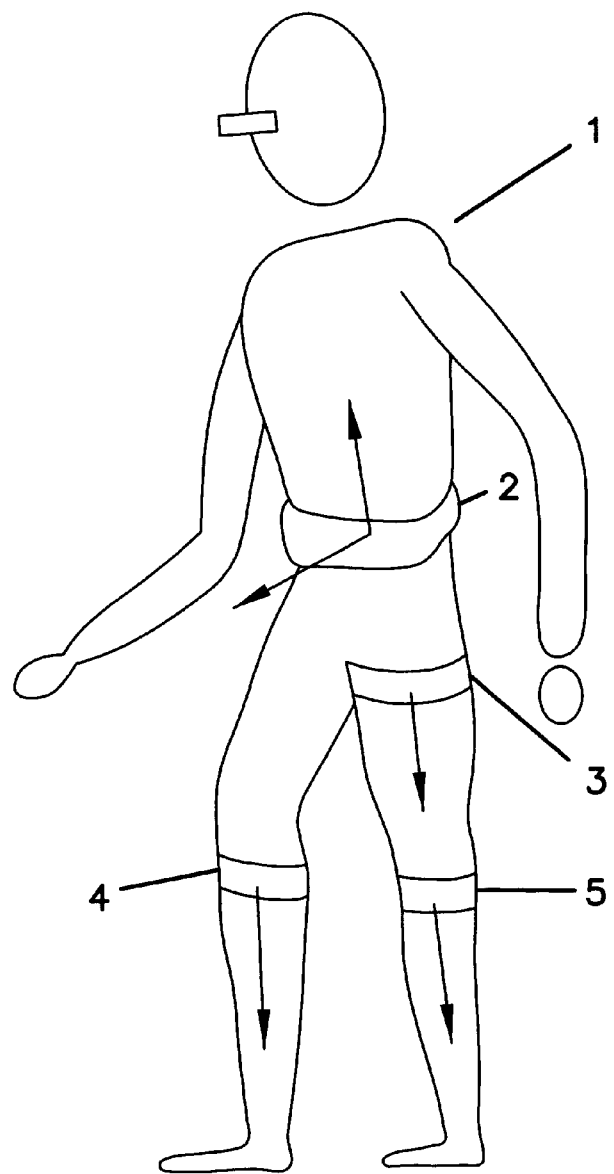
FIG. 1 is a schematic representation of a subject with sensors attached to that subject.

FIG. 1 schematically depicts a subject 1. By way of example, a subject having a disorder of the knee joint has been chosen. The measurements to be performed take place with the aid of sensors to be fastened to the body of the subject. Such sensors can, for instance, be included in respective fastening straps, which are fastened around the waist of the subject (strap 2), around the left upper leg (strap 3), and beneath each of the knee joints (straps 4 and 5).

FIG. 2 shows an example of a score table such as can be used in the examination on the condition of the knee joint of the subject according to FIG. 1.

In the score table of FIG. 2, first some data regarding the individual under examination are recorded, such as the name, gender, date of the operation (if applicable) and the name of the surgeon, as well as the date of the examination and the name of the examiner. The examinations take place, for instance, at predetermined times. The score table further has room for including a summary of those examinations at different times. Under the heading Summary, there is room for the knee score (the total percentage) prior to an operation (PRE), and the respective scores 3, 6 and 12 months after the operation.

The score table further contains a total overview, for a single examination, of the ratios per main function (Locomotion, Rise & Descend, Transfers and Lift and Move Loads) and, within a main function, per activity. In FIG. 2 it is assumed that the examination concerns the examination prior to the operation and the scores as filled in relate to that examination. The score per main function is computed with a suitably programmed computing device from the scores per activity within a main function. In a similar manner, a total score is computed from the scores per main function. In FIG. 2 the total score (Kneescore) is 31%.

Hereinbelow, by way of example, for an individual (X), the determination is described of a movement characteristic (K), a ratio for an activity ($V_A$) and a main function ($V_F$), as well as the total percentage.

Using two signals a and b, respectively coming from two piezoresistive accelerometers arranged mutually orthogonally in the transversal plane and worn around the waist by the, subject, for instance for the activity of walking a distance of 9 meters, the characteristic of movement intensity ($K_{MI}$) is determined with the formula $$K_{MI}=g\sqrt{(a^2+b^2)}-g$$

(with gravitation acceleration g=9.8 m/s$^2$) with $K_{MI,walking\ 9m}$=1.5 m/s$^2$ for individual X.

Figure 3:
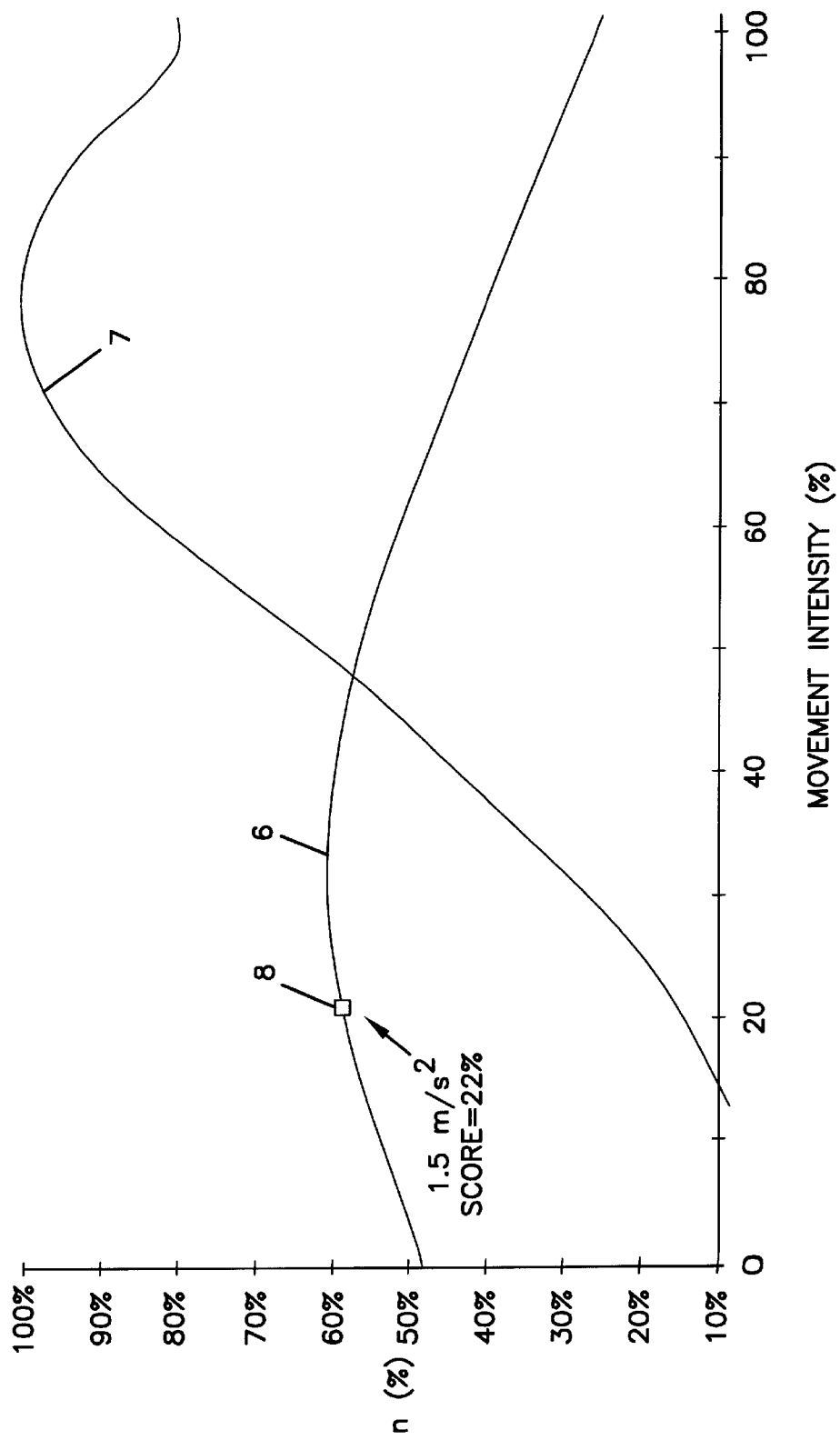
FIG. 3 shows a graph plotting the normal distribution of the movement intensity of a group of healthy standard persons and of a group of standard persons having a comparable disorder to a subject.

In FIG. 3, in a graph in which the movement intensity is plotted in percent for the relative portion of the total population (the area under the curve), the curve 7 represents the assumed normal distribution of the characteristic of movement intensity of a group of healthy standard persons ($N_0$) and the curve 6 represents the assumed normal distribution of the characteristic of movement intensity of an examined group of standard persons having a comparable disorder ($N_A$), who have been examined at an earlier time. The normal distributions of the standard groups have been effected with the formula $$Y=1/\sqrt{(2\pi e^{(x-\mu)^2/2\sigma^2})}$$

with the statistical parameters $\mu(N_G)$=2.57, $\sigma(N_G)$=0.40, $\mu(N_A)$=1.74 and $\sigma(N_A)$=0.65 m/s$^2$. For the conversion of the movement characteristics in units to ratios, a lower limit for the movement intensity ($L_{MI0}$) is determined with the formula $$L_{MI0}=\mu(N_A)-\sigma(N_A)=0\%$$

and an upper limit ($L_{MIb}$) with the formula $$L_{MIb}=\mu(N_G)+\sigma(N_G)=100\%$$

The lower and upper limits for the standard groups are, respectively, 1.09 and 2.96 m/s². The ratio for movement intensity ($V_{MI}$) is determined with the formula $$V_{MI}=(K_{MI}-L_{MI0})/(L_{MIb}-L_{MI0})$$

with $V_{MI,walking\ 9m}=22\%$ for individual X. In FIG. 3 the cube 8 represents how the movement intensity of individual X while walking a distance of 9 meters relates to the normal distributions of the standard groups.

The ratio for an activity is based on the movement characteristics involving statistically significant differences ($\alpha=0.05$) between the examined healthy standard persons and standard persons having a comparable disorder. For the activity of walking over a distance of 9 meters, the characteristics are; time $K_T$ needed to cover the distance, the time $K_{MT}$ that movement is involved, the movement intensity $K_{MI}$, the movement impact $K_{IM}$, the movement intensity $K_{ATMI}$ of the affected upper leg, the step frequency $K_{SF}$, the movement angle $K_{ATA}$ of the upper leg on the affected side, the movement intensity $K_{ASMI}$ of the affected lower leg, the movement intensity $K_{NSMI}$ of the non-affected lower leg, the forward acceleration during push off with the affected leg ($K_{AFA}$) and with the non-affected leg ($K_{NFA}$). The ratio is determined with the formula $$V_{walking\ 9m}=\mu(K_T, K_{MT}, K_{MI}, K_{IM}, K_{ATMI}, K_{SF}, K_{ATA}, K_{ASMI}, K_{NSMI}, K_{APA}, K_{NFA})$$

with $V_{walking\ 9m}=\mu(70, 65, 22, 24, 0, 55, 6, 27, 26, 15, 36)=31\%$ for individual X. In FIG. 2 this resultant can be read in column 9 m against the activity of Walking under the main function of Locomotion in the overview of the ratios. A similar determination procedure as described above holds for the other ratios for the activities.

Each of the ratios per main function ($V_F$) gives the average of the ratios per activity ($A_1 \ldots A_n$). The main function of locomotion, for instance, is determined with the ratios for walking a distance of 9 meters, walking outside, interval walking (average of 3, 6 and 9 meters) and walking a curve. The ratio for the main functions is determined with the formula $$V_F=\mu(V_{A1} \ldots V_{An})$$

with $V_{locomotion}=\mu(31,0,\mu(54,52,46),37)=29\%$ for individual X.

In FIG. 2, this resultant can be read in the column Average, against Score of the main function Locomotion in the overview of the ratios. The total percentage shown in FIG. 2—at the bottom, right, indicates the average of the ratios per main function.

Figure 4:
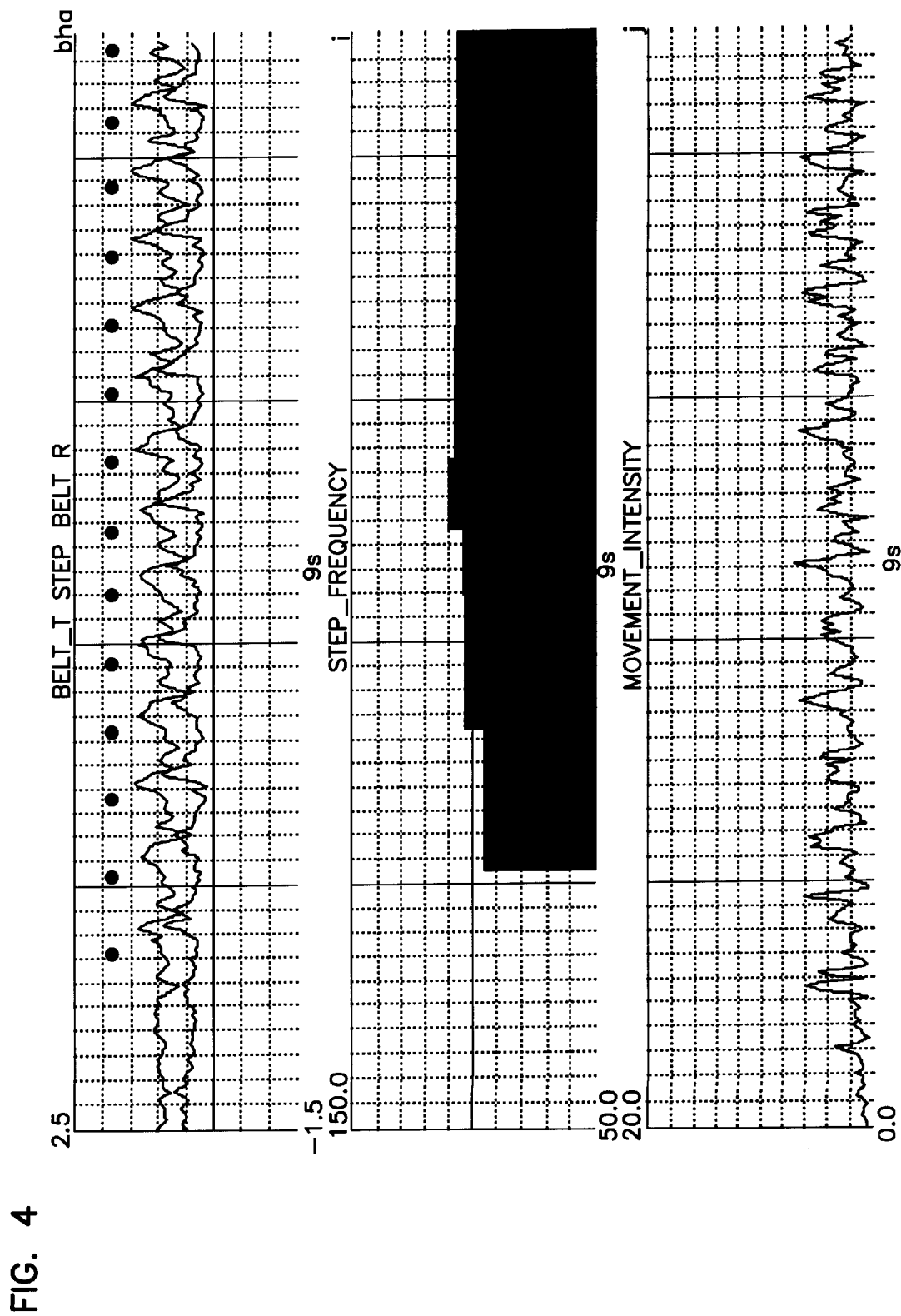
FIG. 4 is a representation of the manner in which measuring data of the sensors carried by a subject are graphically imaged on a monitor.

FIG. 4 represents how the data of the sensors fastened to the body of a subject are imaged graphically on a monitor. Depicted is the screen of the monitor for the part 'walking' of an examination on the condition of a knee of the subject. The various measuring values are entered in a suitably programmed computing device and compared to the measuring values of pre-selected standard groups, to compute ratios therefrom.

Figure 5:
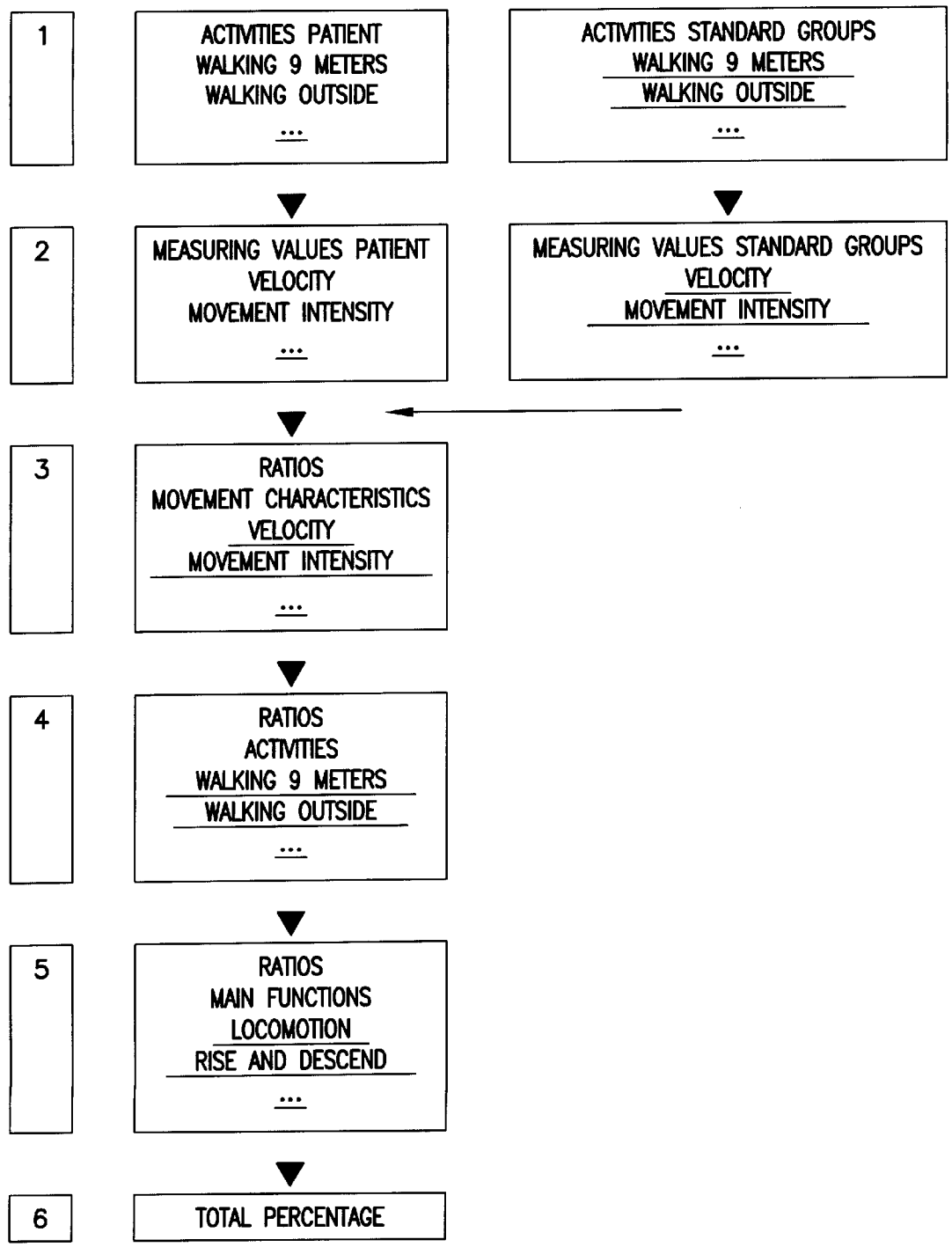
FIG. 5 is a flow diagram of an embodiment of the method according to the invention.

FIG. 5 shows a flow diagram of an embodiment of the method according to the invention. In step 1 it is determined which activities the patient will perform within the various main functions. Within the main function of locomotion, those activities will include walking over a distance of 9 meters and walking outside. Other activities are indicated by a dotted line in step 1. The activities of the patient will be compared to corresponding activities of the selected standard groups. This is indicated in the right-hand column at step 1.

As represented in step 2, for each activity, measuring values are determined for the patient. For the activity of walking, those measuring values comprise values regarding the characteristics of velocity and movement intensity, as mentioned, and many others, as indicated by the dotted line. For the same characteristics, for the same activity, measuring values of standard groups are available. These measuring values have been previously determined. The availability of reference measuring values is indicated in is the right-hand column at step 2.

In step 3 the measuring values of the movement characteristics of the patient and those of the standard groups are compared to each other and ratios are computed for each movement characteristic. In step 4 the ratios of the movement characteristics are averaged per activity to determine a ratio for each activity. In step 5 the ratios of the activities are averaged per main function to determine a ratio for each main function. Thus the ratios for walking a 9-meter distance, walking outside and the other activities indicated by the dotted line in step 4 within the main function of locomotion lead to a ratio for that main function of locomotion.

In step 5 it is indicated that thus ratios are obtained for the main functions of locomotion, rise & descend, and other main functions represented by a dotted line. In step 6, finally, by averaging, a total percentage is computed from the ratios for the main functions.

What is claimed is:

1. A method for measuring and indicating, in the form of an indication on a predetermined scale of comparison, the extent to which an individual is limited in daily life activities, comprising:

measuring, with the aid of at least one sensor to be fastened to the body of the individual to be examined, postures, movements or motional changes of the body or parts of the body of the individual in a selected number of motor activities to be performed by the individual;

wherein the measuring data of the at least one sensor are inputted into a suitably programmed computing device, where those data, as far as necessary, are converted into data concerning position or movement or motional change of the body or parts of the body, and are subsequently compared to corresponding reference data inputted into the computing device, coming from one or more standard persons or standard groups, in order to determine per measurement or series of measurements a percentage or ratio indicating the extent to which the individual is limited as regards the activity in question.

2. A method according to claim 1, wherein for a number of physical activities of the kind that are performed daily, and divided over a number of main functions, determining ratios for a number of movement characteristics per activity and then averaged at least per activity, in order to determine a percentage or ratio for each of those activities;

followed by determining from the ratios of activities belonging to one main function a ratio for that main function; and determining from the ratios for each of the number of main functions one total percentage or total ratio which is representative of the total limitation in daily life activities, the total function, of the individual in question.

3. A method according to claim 2, wherein the measuring steps are performed on activities selected from at least each of the groups of locomotion, rise and descend, transfer, lifting and moving loads.

4. A method according to claim 3, wherein the measuring steps are performed on activities at least comprising walking, climbing stairs, descending stairs, sitting down in a chair, getting up from a chair, lying down on a bed, getting up from a bed, lifting an object and carrying an object.

5. A method according to claim 3, wherein the measuring steps are performed with at least two sensors to be fastened to the body of the individual to be examined.

6. A method according to claim 5, wherein the measuring steps are performed, using a sensor fitted in a strap or other element to be fastened around the waist of the individual to be examined; and using a sensor fitted in a strap or other element to be fastened to a lower or upper leg of the individual to be examined.

7. A method according to claim 2, wherein the measuring steps are performed with at least two sensors to be fastened to the body of the individual to be examined.

8. A method according to claim 7, wherein the measuring steps are performed, using a sensor fitted in a strap or other element to be fastened around the waist of die individual to be examined, and using a sensor fitted in a strap or other element to be fastened to a lower or upper leg of the individual to be examined.

9. A method according to claim 1, wherein the measuring steps are performed on activities selected from at least each of the groups of locomotion, rise and descend, transfer, lifting and moving loads.

10. A method according to claim 9, wherein the measuring steps are performed with at least two sensors to be fastened to the body of the individual to be examined.

11. A method according to claim 10, wherein the measuring steps are performed, using a sensor fitted in a strap or other element to be fastened around the waist of the individual to be examined; and using a sensor fitted in a strap or other element to be fastened to a lower or upper leg of the individual to be examined.

12. A method according to claim 9, wherein the measuring steps are performed on activities at least comprising walking, climbing stairs, descending stairs, sitting down in a chair, getting up from a chair, lying down on a bed, getting up from a bed, lifting an object and carrying an object.

13. A method according to claim 12, wherein the measuring steps are performed with at least two sensors to be fastened to the body of the individual to be examined.

14. A method according to claim 13, wherein the measuring steps are performed, using a sensor fitted in a tap or other element to be fastened around the waist of the individual to be examined; and using a sensor fitted in a strap or other element to be fastened to a lower or upper leg of the individual to be examined.

15. A method according to claim 1, wherein the measuring steps are performed with at least two sensors to be fastened to the body of the individual to be examined.

16. A method according to claim 15, wherein the measuring steps are performed, using a sensor which is fitted in a strap to be fastened around the waist of the individual to be examined; and using a sensor fitted in a strap or other element to be fastened to a lower or upper leg of the individual to be examined.

* * * * *